(12) United States Patent
Frye et al.

(10) Patent No.: US 8,419,783 B2
(45) Date of Patent: Apr. 16, 2013

(54) GRAFT DEPLOYMENT ASSIST TOOL

(75) Inventors: Mark R. Frye, Bloomington, IN (US);
William F. Moore, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 132 days.

(21) Appl. No.: 12/831,725

(22) Filed: Jul. 7, 2010

(65) Prior Publication Data

US 2012/0010692 A1   Jan. 12, 2012

(51) Int. Cl.
*A61F 2/84* (2006.01)
*A61M 5/00* (2006.01)

(52) U.S. Cl.
USPC .................................. 623/1.11; 604/164.01

(58) Field of Classification Search .............. 623/1.11; 604/103.2–103.5; 606/191; 128/898
See application file for complete search history.

(56) References Cited

U.S. PATENT DOCUMENTS

| | | | |
|---|---|---|---|
| 6,537,254 B1 | 3/2003 | Schock et al. | |
| 7,172,580 B2 * | 2/2007 | Hruska et al. | 604/248 |
| 7,226,433 B2 * | 6/2007 | Bonnette et al. | 604/164.01 |
| 2005/0060018 A1 * | 3/2005 | Dittman | 623/1.11 |
| 2005/0065590 A1 * | 3/2005 | Shelso | 623/1.11 |
| 2006/0282155 A1 | 12/2006 | Fearn et al. | |
| 2007/0078395 A1 * | 4/2007 | Valaie | 604/164.01 |
| 2007/0185558 A1 * | 8/2007 | Hartley | 623/1.11 |
| 2007/0191775 A1 | 8/2007 | Diep et al. | |
| 2007/0276461 A1 * | 11/2007 | Andreas et al. | 623/1.11 |
| 2008/0065011 A1 * | 3/2008 | Marchand et al. | 604/103.02 |
| 2008/0200943 A1 * | 8/2008 | Barker et al. | 606/192 |
| 2009/0149938 A1 * | 6/2009 | Grewe et al. | 623/1.11 |
| 2009/0171427 A1 | 7/2009 | Melscheimer et al. | |
| 2010/0004730 A1 | 1/2010 | Benjamin et al. | |
| 2010/0204684 A1 * | 8/2010 | Garrison et al. | 606/1 |
| 2011/0054585 A1 * | 3/2011 | Osborne | 623/1.11 |
| 2011/0301640 A1 * | 12/2011 | Pai et al. | 606/213 |
| 2012/0041371 A1 * | 2/2012 | Tal et al. | 604/164.08 |
| 2012/0310166 A1 * | 12/2012 | Huff | 604/167.03 |

OTHER PUBLICATIONS

European extended search report completed Oct. 27, 2011 for EPO11172924, 5 pgs.

* cited by examiner

*Primary Examiner* — Suzette J Gherbi
(74) *Attorney, Agent, or Firm* — Brinks Hofer Gilson & Lione

(57) ABSTRACT

A delivery system for a medical device may include a sheath, a catheter slideably disposed within the sheath, and a hemostatic device comprising a housing disposed around and sealingly engaged with the sheath by a first seal. A sleeve is slideably coupled to the catheter and comprises a second seal sealingly engaging the catheter. The sleeve is movable between a first position, in which the sleeve is disposed outside of the housing and the first seal is sealingly engaged with an outer surface of the catheter, and a second position in which at least a portion of the sleeve is disposed within the housing between an inner surface of the housing and the outer surface of the catheter, wherein, in the second position, the first seal is sealingly engaged with an outer surface of the sleeve and the second seal is sealingly engaged with the outer surface of the catheter.

21 Claims, 6 Drawing Sheets

GRAFT DEPLOYMENT ASSIST TOOL

BACKGROUND

1. Field of the Invention

This invention relates to medical devices and, in particular, to delivery systems for placement of a prosthesis in a body lumen.

2. Description of Related Art

Endoluminal prostheses, such as stents and stent grafts, are used for treating damaged or diseased body lumens such as the esophagus, bile duct, and blood vessels. For example, endoluminal prostheses may be used for repairing the diseased aorta including abdominal aortic aneurysms, thoracic aortic aneurysms, and other such aneurysms. The prosthesis is placed inside the body lumen and provides some or all of the functionality of the original, healthy vessel.

The deployment of endoluminal prostheses into the lumen of a patient from a remote location by the use of a catheter delivery and deployment device is well known in the art. For example, PCT Publication No. WO 98/53761 entitled "A Prosthesis and a Method and Means of Deploying a Prosthesis," which is incorporated herein by reference, proposes a delivery and deployment system for an endoluminal prosthesis. The prosthesis is radially compressed onto a delivery catheter and is covered by an outer sheath. To deploy the system, the operator slides the outer sheath over the delivery catheter, thereby exposing the prosthesis. The prosthesis expands outwardly upon removal of the sheath. Such a delivery and deployment device has been referred to as a "push-pull" system because as the operator pulls the sheath proximally in relation to the delivery catheter, the delivery catheter "pushes" the prosthesis out of the sheath.

With some catheter delivery and deployment devices, the force required to withdraw the sheath may be relatively high. The withdrawal force is a function of various factors including, for example, frictional resistance caused by the sliding engagement between components of the system such as the outer sheath, the delivery catheter, the prosthesis, and a hemostatic valve assembly. A delivery and deployment device may require as much as 100 Newtons or approximately 22.5 pounds of force to deploy. This force is typically provided by the physician performing the procedure. Such high force may tire an operator or result in inaccurate placement of the medical device.

SUMMARY

Medical device deployment systems are described which may reduce the amount of force required to deploy a medical device within a body lumen or cavity. The embodiments may include any of the following aspects in various combinations and may also include any other aspect described below in the written description or in the attached drawings.

In one aspect, the delivery system may include a sheath having a lumen extending along a central axis thereof, a catheter slideably disposed within the lumen, a hemostatic device comprising a housing disposed around and sealingly engaged with the sheath, with the housing including a first seal, and a sleeve slideably coupled to the catheter. The sleeve includes a second seal that is sealingly engaged the catheter. The sleeve is movable between a first position in which the sleeve is disposed outside of the housing and the first seal is sealingly engaged with an outer surface of the catheter, and a second position in which at least a portion of the sleeve is disposed within the housing between an inner surface of the housing and the outer surface of the catheter. In the second position, the first seal is sealingly engaged with an outer surface of the sleeve and the second seal is sealingly engaged with the outer surface of the catheter. When the sleeve is in the first position the first seal exerts a first sealing force on the catheter that effects a first frictional resistance between the hemostatic device and the catheter. When the sleeve is in the second position the second seal of the sleeve exerts a second sealing force on the catheter that effects a second frictional resistance between the hemostatic device and the catheter. The second frictional resistance is less than the first frictional resistance, thereby reducing a force necessary to effect relative movement between the sheath and the catheter.

In another aspect, the delivery device may also include an expandable prosthesis disposed on a distal portion of the delivery catheter and within the lumen of the sheath.

A method of reducing a force necessary to effect movement between a sheath an a catheter to which the sheath is sealingly engaged may include: providing a delivery device comprising a sheath having a lumen extending along a central axis thereof, a catheter slideably disposed within the lumen, a hemostatic device comprising a housing disposed around and sealingly engaged with the sheath, where the housing comprising a first seal that exerts a first sealing force against an external surface of the catheter that effects a first frictional resistance to relative movement between the catheter and the housing; and advancing a sleeve over the catheter and through the first seal of the housing, whereby the first seal is decoupled from the catheter and sealingly engages an outer surface of the sleeve, such that the sleeve at least partially isolates the catheter from the first sealing force, wherein the sleeve comprises a second seal that applies a second sealing force against the external surface of the catheter that effects a second frictional resistance to relative movement between the catheter and the housing. The second frictional resistance is less than the first frictional resistance, thereby reducing the force necessary to effect relative movement between the catheter and the sheath.

The foregoing paragraphs have been provided by way of general introduction, and are not intended to limit the scope of the following claims. The described embodiments will be best understood by reference to the following detailed description taken in conjunction with the accompanying drawings.

BRIEF DESCRIPTION OF THE DRAWINGS

The embodiments may be more fully understood by reading the following description in conjunction with the drawings, in which:

FIG. 3(*b*) is a perspective view of the seal of FIG. 3(*a*);

FIG. 3(*c*) is a cross-sectional view of a seal of the hemostatic device of FIG. 2 taken along the line X-X after the hemostatic device is inserted over the catheter of the delivery system;

FIG. 3(*d*) is a perspective view of the seal of FIG. 3(*c*) after the hemostatic device is inserted over the catheter of the delivery system;

FIG. 4(*b*) is a cross-sectional view of the deployment assist device of FIG. 4(*a*);

DETAILED DESCRIPTION

Throughout this specification, the terms "distal" and "distally" refer to a position, direction, or orientation that is generally away from the patient. Accordingly, the terms "proximal" and "proximally" refer to a position, direction, or orientation that is generally toward the patient.

Figure 1:
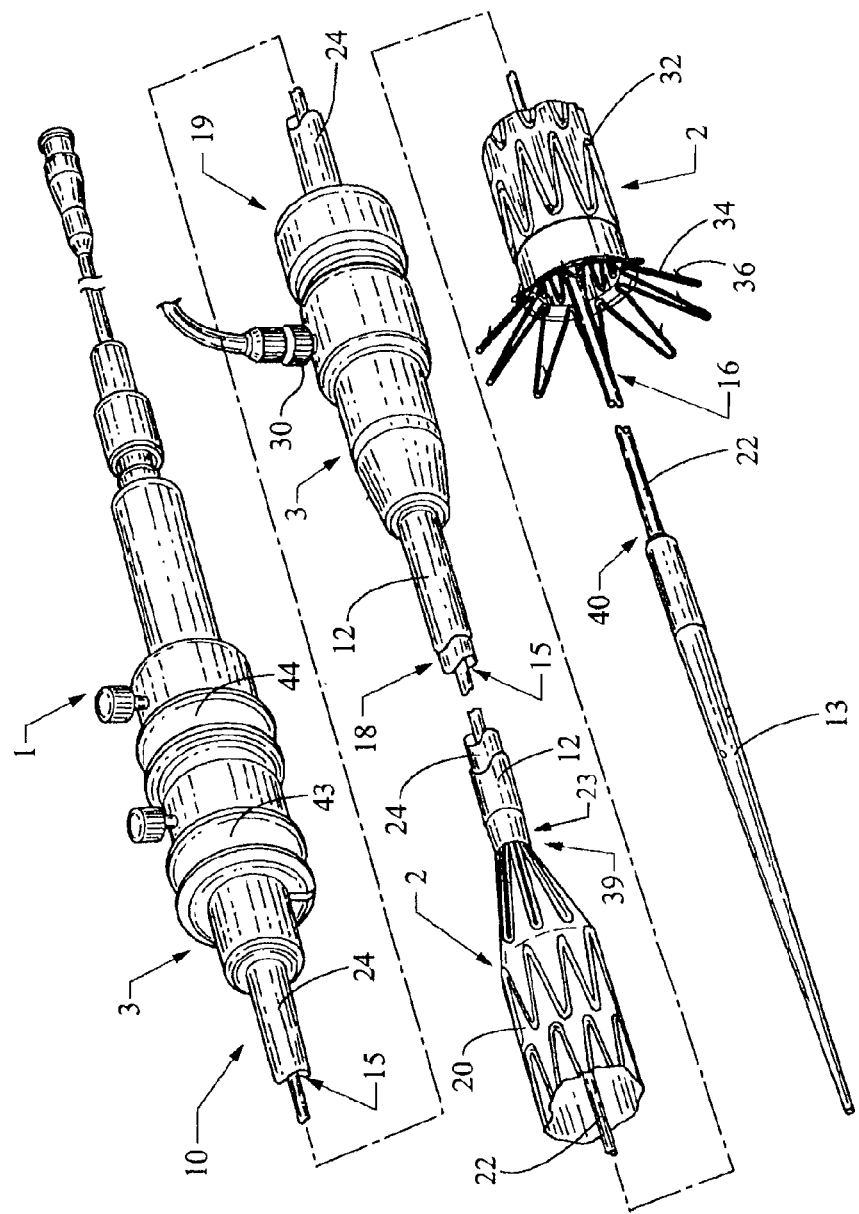
FIG. 1 is a plan view of a delivery system for a medical device.
Figure 2:
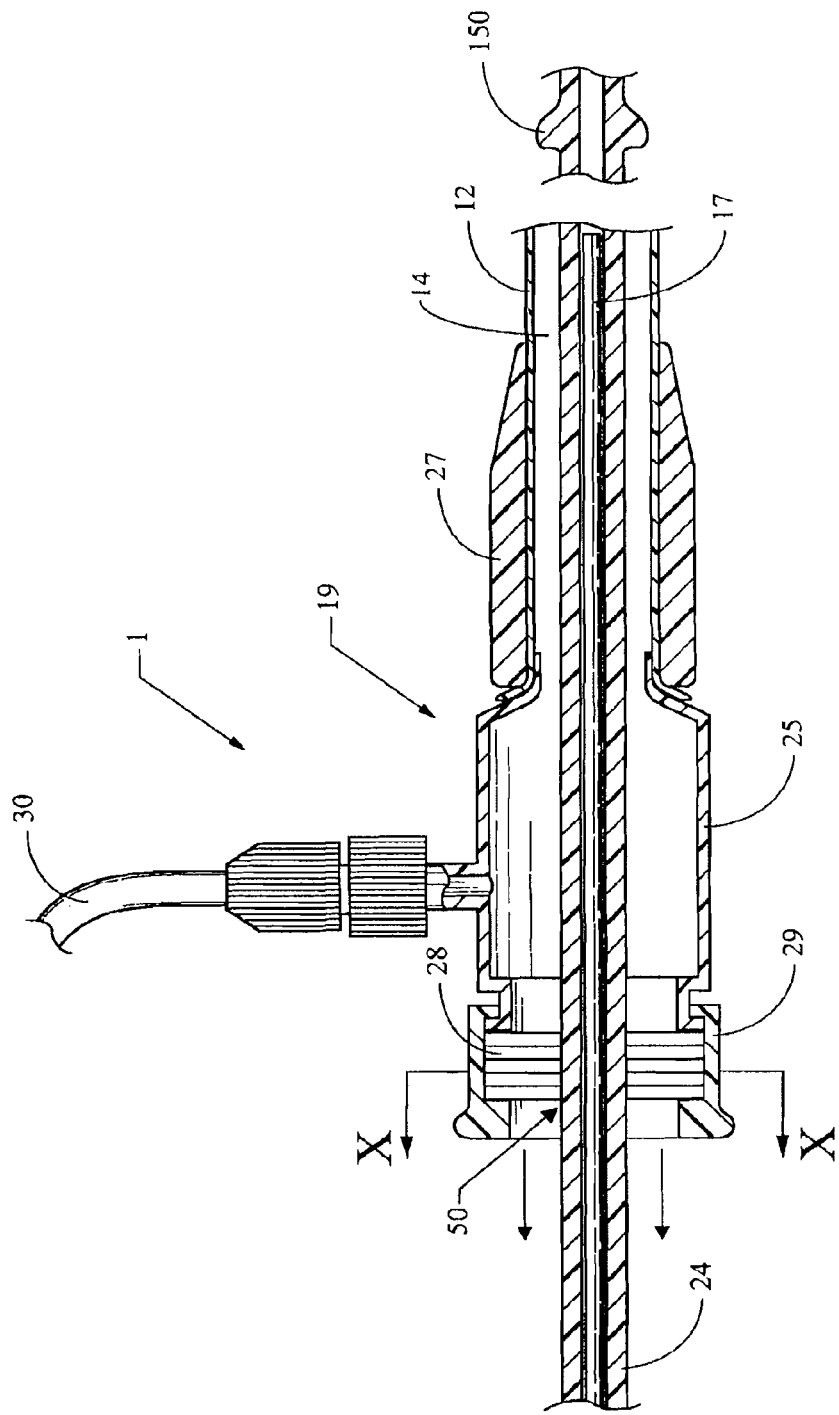
FIG. 2 is a side cross-sectional view of a hemostatic device of the delivery system of FIG. 1.

Referring now to the figures, FIGS. 1-3 illustrate an embodiment of a delivery system for delivering and deploying a medical device. The delivery system 1 may include a delivery catheter 10 and a sheath 12. In operation, the delivery catheter 10 and the sheath 12 are configured to selectively retain and release an expandable prosthesis 20. The delivery catheter 10 has a proximal end and a distal end.

A dilator head 13 is disposed at the distal end of the delivery catheter. The dilator head 13 is tapered in the distal direction to provide for a smooth, atraumatic transition from a guide wire over which the delivery system is advanced into a body lumen or cavity. A guidewire lumen 15 extends longitudinally through the delivery catheter 10 between the proximal and distal ends. The delivery catheter 10 is configured to receive a guidewire 17 via the guidewire lumen 15 as shown in FIG. 2. The delivery catheter 10 also includes a prosthesis receiving portion 16 and a prosthesis release portion 18, as shown in FIG. 1. The receiving portion 16 is disposed on a distal portion of the delivery catheter 10 and is configured to receive the prosthesis 20 in a radially compressed configuration. As shown in FIG. 1, the receiving portion 16 may include a catheter 22 having a longitudinally uniform external diameter.

The release portion 18 of the delivery catheter 10 is disposed generally proximally of the prosthesis 20. The release portion 18 can be manipulated, along with the sheath 12, to selectively deliver and deploy the prosthesis 20 in the body lumen. As shown in FIG. 1, the release portion 18 may include a dilator catheter 24 having a longitudinally uniform external diameter. The diameter of the dilator catheter 24 may be larger than the diameter of the catheter 22. The release portion 18 may include a distal-facing annular abutment surface at the transition between catheters 22 and 24. The annular abutment surface faces the proximal end of the prosthesis 20 and is configured to contact the proximal end of the prosthesis 20 during deployment, thereby holding the prosthesis 20 in place at a treatment site within a body lumen or cavity when the sheath 12 is withdrawn in the proximal direction. Stated differently, the abutment surface acts as a reaction surface which allows the delivery catheter 10 to push the prosthesis 20 distally as the sheath 12 is pulled proximally relative to the catheters 22 and 24. The delivery catheter 10 may be formed as a single unitary monolithic structure. Alternatively, the delivery catheter 10 may be formed of a plurality of slideably interconnected catheters 22, 24.

The sheath 12 includes an elongate tubular body having a wall thickness and a proximal and distal end. An inner surface of sheath 12 defines a lumen 14 extending along a longitudinal axis thereof. The lumen 14 may have a generally constant diameter along its length. The sheath 12 extends proximally from the delivery section 2 to the user manipulation section 3. The delivery catheter 10 is slideably disposed within the lumen 14. The sheath 12 may slideably cover and restrain the prosthesis 20 onto the catheter 22 in a radially compressed configuration in which the diameter of the prosthesis 20 is reduced as compared to its unrestrained state. The dilator head 13 may have a recessed portion disposed at its proximal end that is shaped to receive the distal end of the sheath 12 and form a generally smooth transition therebetween so as to prevent trauma to the body lumen or cavity as the delivery catheter 10 is advanced into the patient for delivery and deployment. The proximal end of the sheath 12 may be configured to remain outside of the body during the procedure, in which case the sheath 12 may be directly manipulated by the operator to deploy the prosthesis 20.

The sheath 12 may have a length, as shown in FIG. 1, that is significantly greater than the length of the prosthesis 20. For example, the sheath 12 may have a length that is two or more times greater than the length of the prosthesis 20. Alternatively, the sheath 12 may have a length that is generally equal to or only somewhat greater than the length of the prosthesis. The sheath 12 may have a uniform internal diameter. The internal diameter may be substantially equal to the external diameter of the catheter 24 such that the inner surface of the sheath 12 slideably engages the delivery catheter 10.

The sheath may be made of any suitable biocompatible material, for example PTFE, nylon, or polyethylene. The sheath may optionally include a flat wire coil to provide the sheath with increased pushability and kink-resistance as the sheath is advanced through the body lumen or cavity, as discussed in U.S. Pat. No. 5,380,304 and U.S. Published Patent Application No. 2001/0034514 A1, which are incorporated herein by reference in their entirety.

As shown in FIG. 1, the prosthesis 20 may include a stent graft having a plurality of self-expanding stents 32. Self-expanding stents may be made of stainless steel, materials with elastic memory properties, such as NITINOL, or any other suitable material. A suitable self-expanding stent includes Z-STENTS®, which are available from Cook Incorporated, Bloomington, Ind., USA. When the sheath 12 is removed, the compressed stents 32 cause the prosthesis 20 to expand. The prosthesis 20 also may include an anchor, such as an exposed strut 34, for anchoring the prosthesis 20 in the body lumen. As shown in FIG. 1, the stent 34 may be formed from a single or multiple wires having zigzag shape and may comprise barbs 36, or other anchoring mechanisms, that extend from the stent. When the anchor 34 is released, the barbs 36, or other anchoring mechanisms, engage the surrounding lumen and help prevent migration of the stent after implantation in the body lumen or cavity. However, it should be understood that the stents 32 and anchor(s) 34 are not limited to self-expanding configurations and may be balloon expandable. In this case, the delivery system also includes one or more balloons disposed within the sheath to expand the stents 32 or anchors 34 against an inner surface of the body lumen or cavity. Balloon-expandable stents may be made of various materials including, but not limited to, stainless steel (typically 316LSS, CoCr, Etc.).

The stents 32 may cover and/or may be at least partially covered by a graft material. Various graft materials and configurations may be used. Suitable graft configurations include, but are not limited to films, coatings, sheets of biocompatible fabrics, non-woven materials and porous materials. Examples of suitable graft materials include polyesters, such as poly(ethylene terephthalate), polylactide, polyglycolide and copolymers thereof; fluorinated polymers, such as polytetrafluoroethylene (PTFE), expanded PTFE and poly (vinylidene fluoride); polysiloxanes, including polydimethyl siloxane; polyurethanes, including polyetherurethanes, polyurethane ureas, polyetherurethane ureas, polyurethanes containing carbonate linkages and polyurethanes containing siloxane segments, and bioremodelable materials, such as small intestine submucosa ("SIS").

As set forth above, the prosthesis 20 may be retained in a radially reduced configuration between the delivery catheter 10 and the sheath 12. The sheath 12 is slideably disposed over the prosthesis 20 and the delivery catheter 10 such that the sheath 12 is movable in a proximal and a distal direction. In operation, the sheath 12 is withdrawn in the proximal direction by sliding the sheath 12 with respect to the delivery catheter 10 and the prosthesis 20 to expose the prosthesis 20. While the sheath 12 is withdrawn proximally, the operator applies pressure to the delivery catheter 10 in the distal direction via the catheter 24. As the catheter 24 is advanced the abutment surface 23 contacts the proximal end of the prosthesis 20 and pushes the prosthesis 20 in the distal direction while the sheath 12 slides proximally in relation thereto. As the sheath 12 slides proximally, the catheter 24 pushes the prosthesis 20 distally from the receiving portion 16 and into the body lumen or cavity.

The delivery and deployment device 1 may also include proximal and distal deployment control mechanisms 39, 40 as shown in FIG. 1. The proximal control mechanism 39 releasably retains the proximal end of the prosthesis 20 and the distal control mechanism 40 releasably retains the distal end of the prosthesis 20. The proximal control mechanism 39 may include at least one trigger wire that releasably couples the proximal end of the prosthesis 20 to the delivery catheter 10. Likewise, the distal control mechanism 40 may include at least one trigger wire that releasably couples the distal end of the prosthesis 20 to the delivery catheter 10. The trigger wires preferably extend promimally to the external manipulation section 3 where they are coupled to trigger release devices 43, 44. The trigger release devices 43, 44 are configured to selectively decouple the proximal and distal ends of the prosthesis from the delivery catheter 10, respectively. Various prosthesis retention devices, configurations, and methods may be used, for example, those described in PCT Publication No. WO 98/53761, which is incorporated by reference herein.

The delivery and deployment device 1 may further include a hemostatic valve assembly 19, as shown in FIGS. 1-3. The valve assembly may include a housing 25 and a clamping collar 27 that sealingly attaches the housing 25 to the sheath 12. A valve or valve 28 is disposed within the housing 25 between the sheath 12 and the catheter 24. The valve 28 is fixedly connected to the housing 25 and is slideably disposed with respect to the catheter 24. During a procedure, the valve 28 sealingly engages the catheter 24 to control blood loss between the delivery catheter 10 and the sheath 12. The hemostatic sealing device 19 may also include a side tube 30 that facilitates the introduction of medical reagents between the delivery catheter 10 and the sheath 12.

The delivery and deployment device 1 may also include proximal and distal deployment control mechanisms 39, 40 as shown in FIG. 1. The proximal control mechanism 39 releasably retains the proximal end of the prosthesis 20 and the distal control mechanism 40 releasably retains the distal end of the prosthesis 20. The proximal control mechanism 39 may include at least one trigger wire (not shown) that releasably couples the proximal end of the prosthesis 20 to the delivery catheter 10. Likewise, the distal control mechanism 40 may include at least one trigger wire (not shown) that releasably couples the distal end of the prosthesis 20 to the delivery catheter 10. The trigger wires preferably extend proximally to the external manipulation section 3 where they are coupled to trigger release devices 43, 44. The trigger release devices 43, 44 are configured to selectively decouple the proximal and distal ends of the prosthesis from the delivery catheter 10, respectively. Various prosthesis retention devices, configurations, and methods may be used, for example, those described in PCT Publication No. WO 98/53761, which is incorporated by reference herein.

Figure 3A:
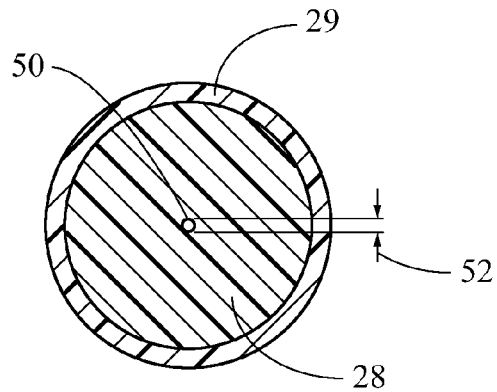
FIG. 3(*a*) is a cross-sectional view of a seal of the hemostatic device of FIG. 2 taken along the line X-X prior to insertion over a catheter of the delivery system.
Figure 3B:
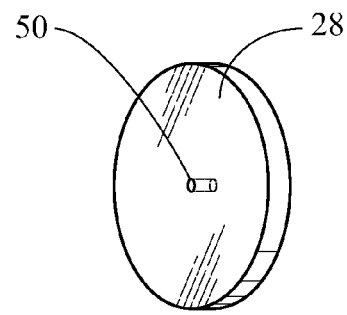
Figure 3C:
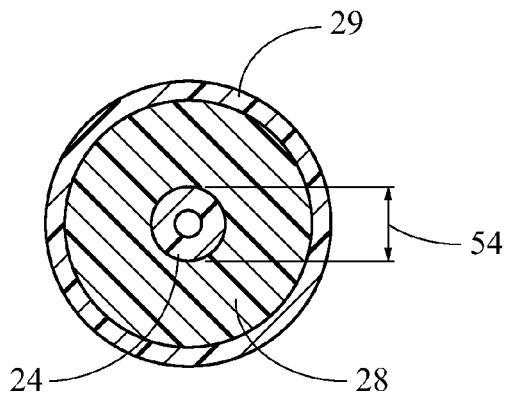
Figure 3D:
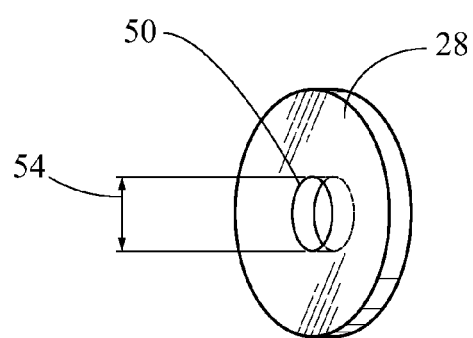

A primary function of the valve assembly 19 is controlling and limiting blood loss during a procedure. Accordingly, the valve 28 forms a tight sealing engagement with the catheter 24. A tight seal may be provided, for example, by providing sufficient area of surface contact between the valve 28 and the catheter 24 and by providing sufficient pressure exerted by the valve against the catheter. As shown in FIGS. 3(a) and (b), the pressure exerted by the valve may be increased by making an aperture 50 through which the catheter 24 is passed as small as possible. The aperture 50 defines a radially inner surface of the valve 28 that is configured to contact and sealingly engage an outer surface of the catheter 24. In some embodiments, the aperture 50 may be a slit that is self sealing when nothing is inserted therethrough. In other embodiments, the aperture 50 may have an annular shape with a diameter 52 of one millimeter or less. In comparison, the diameter of the catheter 24 may have an outer diameter 54 ranging between 12 and 24 French. Thus, in order for the catheter 24 to be passed through a lumen or slit of the aperture 50 in the seal(s) 28, the aperture 50 must stretch in a radially outward direction until the diameter 52 of the aperture is substantially the same as the outer diameter of the catheter 54, as shown in FIGS. 3(c) and (d). As the aperture 50 stretches, the valve 28 is compressed between a radially outermost surface, which is in contact with and constrained by a seal housing 29, and the outer surface of the catheter 24. This compression of the valve 28 results in a radially inward compressive sealing force against the outer surface of the catheter 24. The valve 28 may exert a compressive sealing force that results in a frictional force of about 50 to 60 Newtons between the valve 28 and the catheter 24. Consequently, a force of at least 50-60 Newtons may be necessary to effect relative movement between the sheath 12, which is connected to the valve assembly 19, and the catheter 24.

In general, as the quality of the seal improves, the friction between the sheath 12 and the delivery catheter 10 increases, thereby increasing the force required to slide the valve assembly 19 and the attached sheath 12 over the delivery catheter 10. That is, as the inward, compressive force exerted by the valve 28 on the outer surface of the catheter 24 increases, the seal quality also increases. However, the higher the inward, compressive force exerted on the catheter 24 by the valve 28, the higher the frictional force, and therefore the frictional resistance to movement between the catheter 24 and the valve 28. Because the valve assembly 19 is connected to the proximal end of the sheath 12, the valve assembly 19 must be moved in order to effect relative movement between the sheath 12 and the catheter 24. Thus, the frictional resistance between the valve 28 and the catheter 24 may constitute a significant component of the sheath withdrawal force necessary to effect relative movement between the sheath 12 and the catheter 24 and to deploy the prosthesis 20.

However, as discussed above, the valve 28 of the valve assembly 19 is typically configured to provide an adequate sealing force for relatively small diameter components or devices to be inserted therethrough, for example, a guidewire, as well as comparatively large diameter components/devices, such as the catheter 24. Thus, the valve 28 typically exerts a higher force on the catheter 24 than is necessary for normal sealing purposes. Stated differently, the aperture 50 in the valve 28 must be sufficiently small in order to provide an adequate sealing force against a small diameter component, such as a guide wire. Thus, when a larger diameter component, such as the catheter 24, is advanced through the valve 28, the aperture must stretch to accommodate the larger diameter. However, this stretching of the aperture 50 results in a correspondingly higher compressive force on the catheter 24. Assuming the necessary sealing force at the valve/catheter interface is essentially the same as the valve/guidewire interface, it is clear that the higher compressive force exerted on the larger diameter catheter 24 by the valve 28 is higher than the minimum force that is necessary to provide adequate sealing therebetween. This unnecessarily high compressive sealing force results in an unnecessarily high frictional force between the catheter and the sheath 12 via the attached valve assembly 19.

As set forth above, the sheath withdrawal force is typically provided by the operator (e.g. a physician). Thus, as the required sheath withdrawal force increases, it becomes increasingly difficult for the operator to release the prosthesis 20. If the required sheath withdrawal force is too high, it may tire the operator or force the operator to strain and cause sudden or unexpected withdrawal of the sheath 12, thereby causing inaccurate placement of the prosthesis 20. Further, as the sheath withdrawal force increases, it may cause the catheter 24 and/or the prosthesis 20 to compress slightly in the longitudinal or axial direction. This compression cause energy to be stored in the catheter 24 and the prosthesis 20. When the sheath 12 is withdrawn, the stored energy is suddenly released, which may cause the prosthesis 20 to "jump" in the distal direction as it expands, thereby resulting in inaccurate placement. Accordingly, reducing the frictional force between the catheter 24 and the valve 28 of the valve assembly 19 while maintaining adequate sealing force therebetween may be desirable.

Figure 4A:
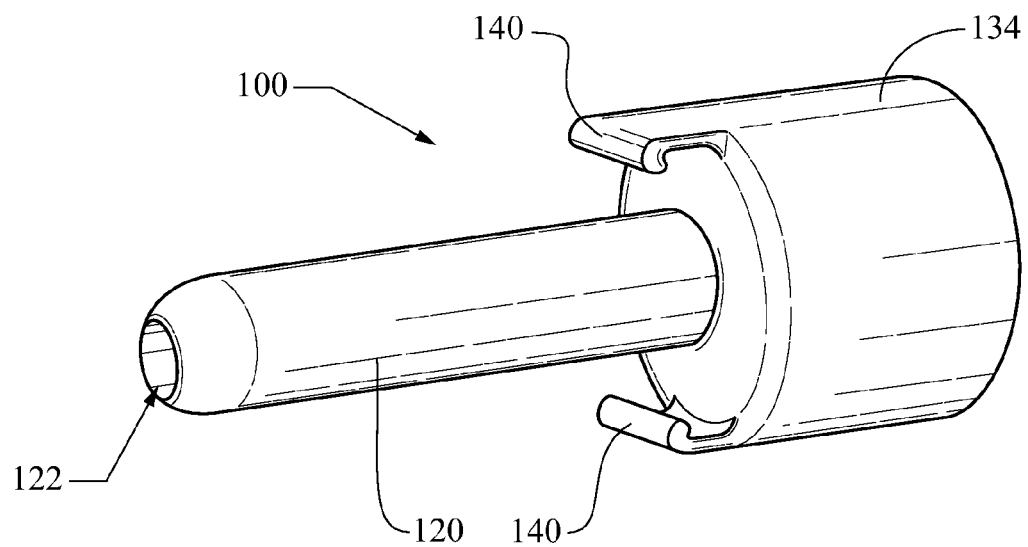
FIG. 4(*a*) is a plan view of a deployment assist device.

FIGS. 4(a) and (b) illustrate an embodiment of a deployment assist device 100. The deployment assist device 100 includes a sleeve 120 having a tapered distal end 122 that extends from the outer diameter 124 to the diameter of a lumen 126 defined by an inner surface of the sleeve 120. The lumen 126 may have a constant diameter that substantially approximates the outer diameter of the catheter 124. In other embodiments, such as the one depicted in FIG. 4(b), the lumen 126 may have a stepped configuration that is narrowest at the proximal and distal ends of the deployment assist device 100 and widest at a central portion thereof. In this embodiment, the portion of the sleeve extending distally from a distal end of the distal seal 132 to the distal end of the sleeve 120 may have a smaller inner diameter 124 and the central portion of the sleeve, which extends from the proximal end of the distal seal 132 to the proximal end of the proximal seal 132, may have a diameter that is increased by an amount 112. Similarly, the lumen 26 may step down in diameter from the proximal end of the proximal seal 132 to the distal end of the deployment assist device 100. In other embodiments, the lumen 126 may have a substantially constant diameter extending the length of the shaft 120. Regardless of whether the lumen 126 has a constant diameter or a stepped diameter, the narrowest portion of the lumen 126 is sized such that it is slightly larger than the outer diameter of the catheter 24. In this way, contact, and therefore friction between the deployment assist device 100 and the inner catheter may be limited to the seal(s) 132.

Figure 4B:
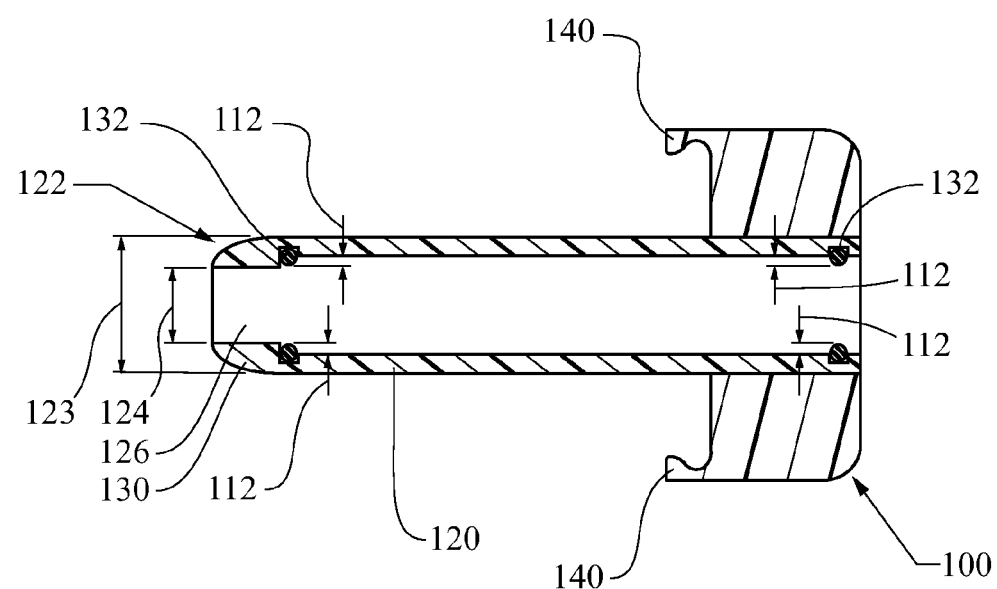

As shown in FIG. 4(b), the proximal and distal seals 132 may extend radially inward slightly beyond the inner surface of the sleeve 120 to provide an interference fit with the catheter 124. When the sleeve 120 is disposed on the catheter 24, the seals 132 are compressed such that they sealingly engage the outer surface of the catheter 24. The seals 132 may exert a sealing force on the catheter 24 of about 25 Newtons to 35 Newtons. However, it should be understood that the device is not limited thereto, and it may exert less than 25 Newtons on the catheter 24, provided that an adequate sealing force is present.

The sleeve 120 may have a constant outer diameter 124, or may vary in diameter along its length. The sleeve 120 may have a housing 134 disposed around a proximal end thereof, as shown in FIGS. 4(a) and (b). Alternatively, the housing 134 may be attached to a proximal end of the sleeve 120. The housing 134 may include an interlocking mechanism 140, such as a catch or other mechanical fixing mechanism that is configured to interface with and couple the deployment assist device 100 to the valve housing 29 or the housing 25 of the valve assembly 19. The sleeve 120 includes at least one seal 132 disposed within an inner lumen defined by the inner surface of the sleeve 120. The seals 132 may be o-ring or disc type seals that are made of an elastic and substantially impermeable material, such as, for example, rubber or silicone. In one embodiment, the sleeve 120 may include two seals 132, with one seal 132 being disposed at proximal and distal portions of the sleeve 120, respectively. As shown in FIG. 4(b), the proximal and distal seals 132 may be disposed in annular grooves formed on the inner surface of the sleeve 120.

Figure 7A:
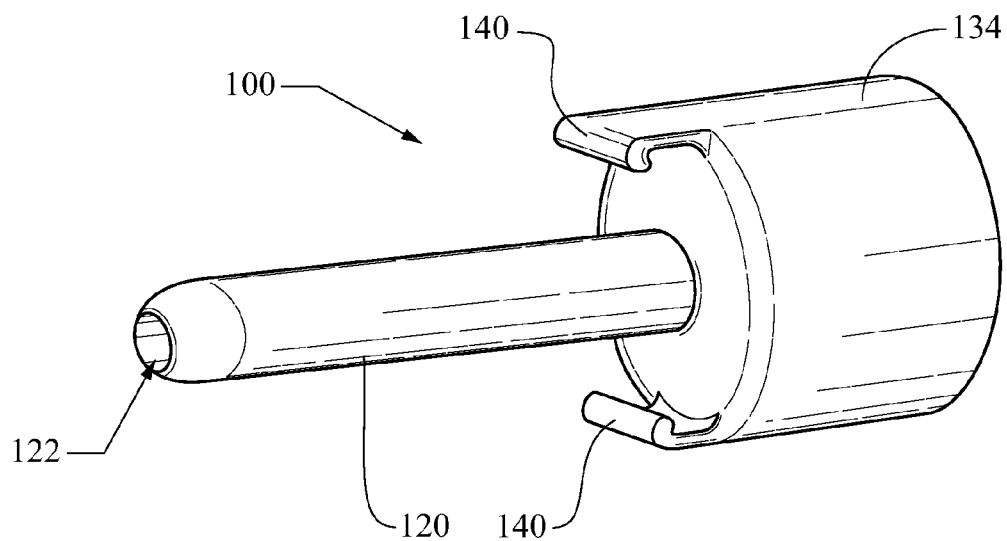
FIG. 7(a) is a plan view of another embodiment of the deployment assist device.
Figure 7B:
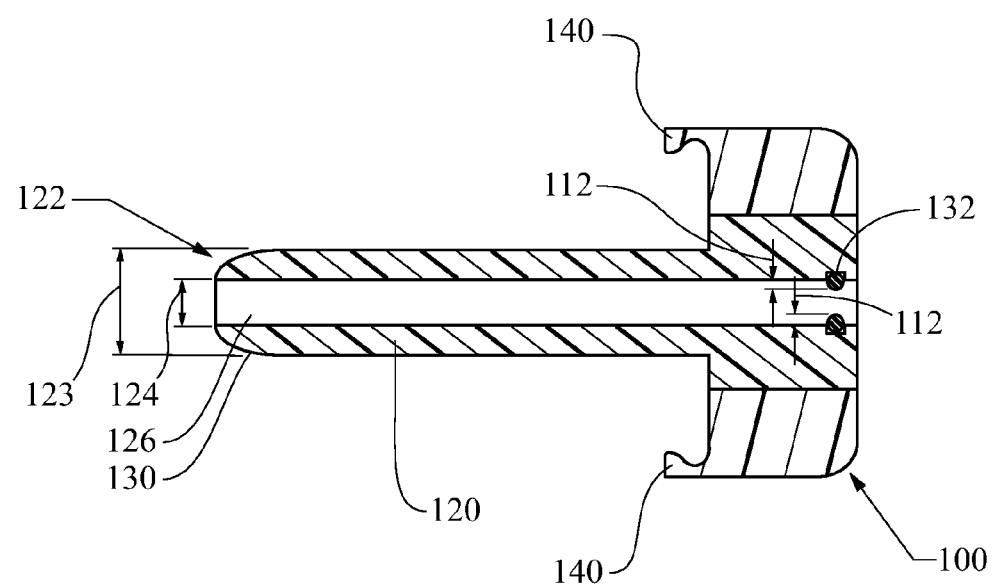
FIG. 7(b) is a cross-sectional view of the deployment assist device of FIG. 7(a).

In another embodiment, shown in FIGS. 7(a) and (b), the sleeve 120 may have an overall thinner diameter and wall thickness to facilitate insertion into the valve assembly 19. In this embodiment, the sleeve 120 is too thin to accommodate a seal 132 at the distal end, thus only a single proximal seal 132 is disposed at the proximal end of the sleeve 129.

The sleeve 120 and the housing 134 may be formed from a lubricious material, for example and without limitation, polytetrafluoroethylene or PTFE (Teflon) to minimize friction between the sleeve 12 and the catheter 24 at any point(s) of contact therebetween.

Figure 5:
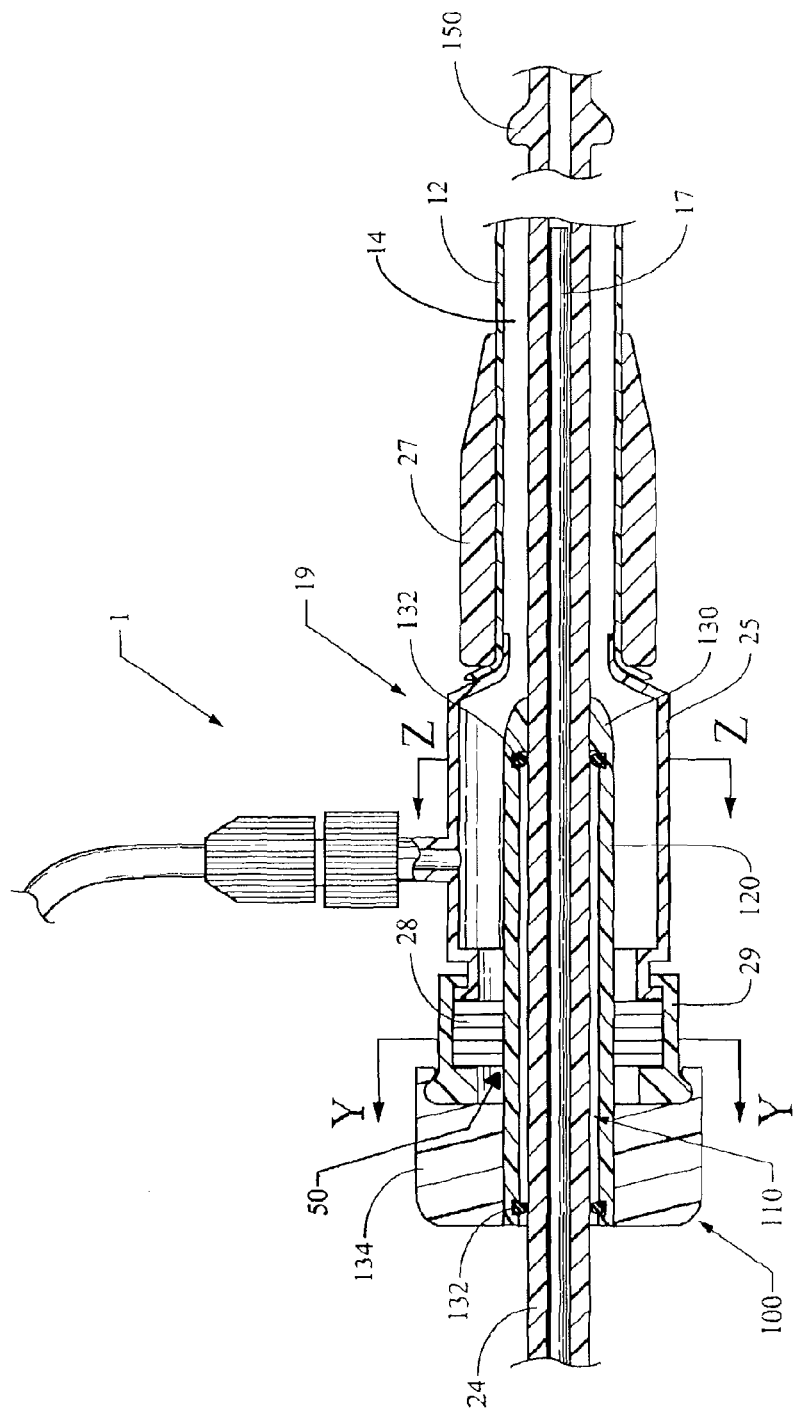
FIG. 5 is a cross-sectional view of the hemostatic device of FIG. 2 including the deployment assist device of FIGS. 4(a) and (b)

In operation, the deployment assist device 100 is advanced over the catheter 24 in the distal direction to the valve assembly 19. Initially, the tapered end 122 of the sleeve 120 contacts the proximal most portion of the valve 28 and facilitates expansion of the aperture 50 as the deployment assist device 100 is advanced through the valve 28 and into the housing 25. The deployment assist device 100 may then be detachably or fixedly coupled to the valve assembly 19. This coupling may be accomplished by advancing the deployment assist device 100 until the interlocking mechanism 140 contacts and engages with a lip or the like disposed on the valve housing 29 in a snap-fit arrangement, as shown in FIG. 5. However, it should be understood that the embodiments are not limited thereto, and any suitable coupling mechanism may be used, for example, threaded engagement mechanisms, mechanical fasteners, or adhesives or the like.

Figure 6A:
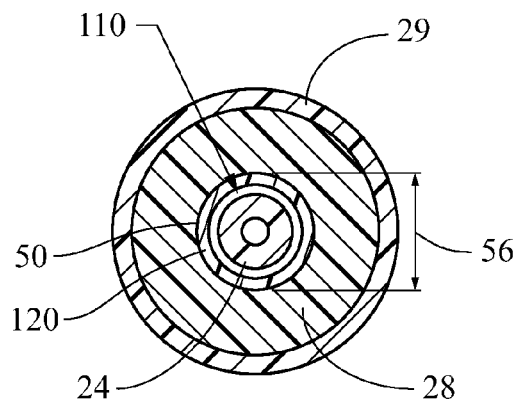
FIG. 6(a) is a cross-sectional view of the seal of the hemostatic device of FIG. 5 taken along the line Y-Y.
Figure 6B:
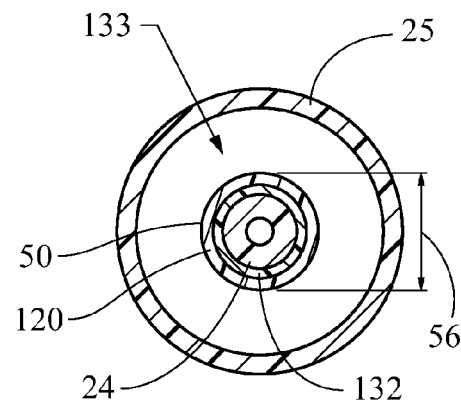
FIG. 6(b) is a cross-sectional view of the delivery system taken along the line Z-Z.

As shown in FIGS. 6(a) and (b), once the sleeve 120 is disposed within the housing 25, the aperture 50 of the valve 28 is sealingly compressed against the outer surface of the catheter 24, while the catheter 24 is sealed against the sleeve 24 by the seal(s) 132 (See FIG. 6(b)). In embodiments having a stepped lumen 126, an annular space 110 may be formed between the inner surface of the sleeve 120 and the outer surface of the catheter 24 in the central portion of the deployment assist device 100 (See FIG. 6(a)).

Because the aperture of the valve 28 must be stretched to an even wider diameter 56 to accommodate the sleeve 120, the sealing force exerted by the valve 28 of the valve assembly 19 may be significantly higher on the sleeve 120 than the normal sealing force exerted on the catheter 24 at the diameter 54 when no deployment assist device 100 is present. Thus, the sealing force exerted on the sleeve 120 by the valve 28 will typically result in a frictional force that is greater than the 50-60 Newtons exerted on the inner catheter 24. The sleeve 120 may be formed from materials having sufficient rigidity to maintain patency of the lumen 126 even when exposed to this increased compressive sealing force applied by the valve 28. Thus, even in embodiments having a constant diameter lumen 126, the deployment assist device 100 may effectively isolate the catheter 24 from the high sealing force exerted by the valve 28 on the sleeve 120. Accordingly, the catheter 24 is only exposed to the sealing force of the seal(s) 132 of the deployment assist device 100. This sealing force is significantly lower than the sealing force exerted by the valve 28 on the catheter 24 when the deployment assist device 100 is not present, and accordingly is also lower than the sealing force exerted by the valve 28 when the deployment assist device 100 is present. For example, the sealing force exerted on the catheter 24 by the seal(s) 132 results in a withdrawal (frictional force) of 25-35 Newtons. In other embodiments, the sheath may partially or substantially shield or isolate the catheter 24 from the high sealing force exerted by the valve 28 on the sleeve 120, resulting in a somewhat lower reduction of the force necessary to withdraw the sheath 12 relative to the catheter 24.

In either case, because the primary component of the frictional force is the normal force exerted on the catheter 24 by the seals 132, the frictional force between the seal(s) 132 of the deployment assist device 100 and the catheter 24 is much lower than the frictional force between the valve 28 and the outer surface of the sleeve 120. Thus, the force necessary to effect movement between the valve assembly 19, and hence the sheath 12, relative to the catheter 24 is significantly reduced as compared to a delivery system without the deployment assist device 100. For example, the sheath withdrawal force may be reduced by about 10% to about 50% of the normal sheath withdrawal force, and in one embodiment, the sheath withdrawal force is reduced by about 25%. In some instances, the deployment assist device 100 may lower the sheath withdrawal force by about 25 Newtons. The amount of reduction in sheath withdrawal force may be influenced by a number of factors, including, for example and without limitation, the materials used to form the sleeve 120 (which affects properties such as rigidity under compression and the like), the valve 28 and the seals 132. Additionally, the size differentials between the aperture 50 of the valve 28, the catheter 24 and the deployment assist device 100 may also influence the amount of reduction in sheath withdrawal force.

Once the sheath 12 has been withdrawn and the prosthesis 20 has been deployed, the inner catheter and other components disposed within the sheath 12 are typically withdrawn through the sheath and the hemostatic valve assembly 19 in the proximal direction to allow the insertion of additional delivery systems or other tools through the valve assembly 19 and the sheath 12. However, when doing so, it is necessary to also remove the deployment assist device 100 in order to maintain the hemostatic seal between the valve assembly 19 and the guidewire 17 once the inner catheter and other larger components have been removed. The deployment assist device 100 may be decoupled from the valve housing 29 or the housing 25 by withdrawing the catheter 24 in the proximal direction while holding the valve assembly 19 and the sheath 12 steady. That is, following deployment of the prosthesis 20, the operator withdraws the catheter 24 relative to the sheath until a step 150 that extends radially outward from the surface of the catheter 24, contacts the distal tapered end 122 of the deployment assist device 100 and causes the interlocking mechanism 140 to become decoupled from the valve housing 29, thus releasing and removing the deployment assist device 100 from the valve assembly 19. In this way, the valve assembly 19 is able to maintain sufficient sealing force and prevent leak paths even after the inner catheter assembly has been removed from the delivery system. In another embodiment, the proximal end of the dilator head 13 may be sized large enough to contact be distal tapered end 122 of the deployment assist device 100 and decouple the deployment assist device 100 from the valve assembly 19 as the inner catheter 24 is withdrawn.

While preferred embodiments have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the features described above are not necessarily the only features of the invention, and it is not necessarily expected that all of the described features will be achieved with every embodiment of the invention.

We claim:

1. A system for delivering and deploying an expandable prosthesis comprising:
    a sheath having a proximal end, a distal end, and a lumen extending between the proximal and distal ends and defining an inner surface;
    a delivery catheter slideably disposed within the lumen and having an outer surface in frictional contact with the inner surface of the sheath lumen;
    an expandable prosthesis disposed on a distal portion of the delivery catheter and within the lumen of the sheath;
    a hemostatic device comprising a housing connected to the proximal end of the sheath and a first seal disposed within the housing and sealingly engaging the delivery catheter; and
    a deployment assist device comprising a sleeve and a second seal disposed within the sleeve that is adapted to sealingly engage the catheter,
    the deployment assist device being movable between a first position in which the sleeve is disposed outside of the hemostatic device housing and the first seal is sealingly engaged with an outer surface of the catheter effecting a first frictional resistance between the housing and the catheter, and a second position in which at least a portion of the sleeve is disposed within the housing between an inner surface of the housing and the outer surface of the catheter,
    wherein, in the second position, the first seal is sealingly engaged with an outer surface of the sleeve and the second seal is sealingly engaged with the outer surface of the catheter and effecting a second frictional resistance between the deployment assist device and the catheter; and
    wherein the second frictional resistance is less than the first frictional resistance between the housing and the catheter, thereby reducing a force necessary to effect relative movement between the sheath and the catheter.

2. A system for delivering and deploying a medical device comprising:
    a housing comprising a first seal;

a catheter having an outer surface and slideably extending through the housing;

a sleeve comprising a second seal;

the sleeve being movable between a first position in which the sleeve is disposed outside of said housing and a second position in which at least a portion of the sleeve is disposed within the housing between an inner surface of the housing and the outer surface of the catheter;

wherein when the sleeve is in the first position the first seal of the housing is sealingly engaged with the outer surface of the catheter and effects a first frictional resistance between the housing and the catheter, and when the sleeve is in the second position the first seal of the housing is sealingly engaged with an outer surface of the sleeve and the second seal of the sleeve is sealingly engaged with at least a portion of the outer surface of the catheter;

wherein the second seal of the sleeve effects a second frictional resistance between the sleeve and the catheter, the second frictional resistance being less than the first frictional resistance.

3. The system of claim 2, further comprising a sheath having a lumen extending along a central axis thereof, the catheter being disposed within the lumen, wherein the housing is disposed around and connected to at least a portion of the sheath.

4. The system of claim 3, wherein a force required to move the sheath relative to the catheter when the sleeve is in the second position is less than a force required to move the sheath relative to the catheter when the sleeve is in the first position.

5. The system of claim 4, wherein, when the sleeve is in the second position, the force required to move the sheath relative to the catheter is reduced by 10% or more.

6. The system of claim 4, wherein, when the sleeve is in the second position, the force required to move the sheath relative to the catheter is reduced by 25% or more.

7. The system of claim 4, wherein, when the sleeve is in the second position, the force required to move the sheath relative to the catheter is reduced by 50% or more.

8. The system of claim 3, further comprising an expandable prosthesis disposed within the lumen of said sheath.

9. The system of claim 3, where the catheter has an outer diameter that approximates an inner diameter of the lumen of the sheath.

10. The system of claim 2, wherein the sleeve comprises a lubricious material.

11. The system of claim 10, wherein the sleeve comprises Teflon.

12. The system of claim 2, wherein the sleeve comprises a tapered end.

13. The system of claim 2, wherein the first seal of said housing comprises at least one disk valve.

14. The system of claim 13, wherein the at least one disk valve comprises a stretchable opening having a diameter of 1 mm or less.

15. The system of claim 14, wherein the at least one disk valve comprises a stretchable opening having a diameter of 0.1 mm or less.

16. The system of claim 2, wherein the first seal comprises a plurality of disk valves.

17. The system of claim 3, wherein an inner surface of the sheath and the outer surface of the catheter are in frictional engagement with each other.

18. The system of claim 2, wherein the housing comprises an interlocking mechanism that reversibly interlocks the housing in relation to the sleeve to limit relative movement therebetween.

19. The system of claim 2 wherein when said sleeve is in the second position the sleeve is attached to at least a portion of the housing.

20. The system of claim 19, where the catheter comprises an increased diameter portion disposed distally of the sleeve in the second position, the increased diameter portion engageable with said sleeve for detaching the sleeve from the housing when the catheter is withdrawn from the sheath.

21. A method of reducing a force necessary to effect movement between a housing and a catheter the method comprising:

providing a delivery device;

the delivery device comprising a housing and a catheter slideably extending through the housing, the housing comprising a first seal that exerts a first sealing force against an external surface of the catheter that effects a first frictional resistance to relative movement between the catheter and the housing; and advancing a sleeve over the catheter and through the first seal of the housing, whereby the first seal is decoupled from the catheter and sealingly engages an outer surface of the sleeve, the sleeve at least partially isolating the catheter from the first sealing force, wherein the sleeve comprises a second seal that applies a second sealing force against at least a portion of the external surface of the catheter that effects a second frictional resistance to relative movement between the catheter and the housing, the second frictional resistance being less than the first frictional resistance.

* * * * *